(12) United States Patent  (10) Patent No.: US 8,184,875 B2
Francke et al.  (45) Date of Patent: May 22, 2012

(54) METHOD FOR CREATING, DISPLAYING, AND ANALYZING X-RAY IMAGES AND APPARATUS IMPLEMENTING THE METHOD

(75) Inventors: Tom Francke, Sollentuna (SE); Christer Ullberg, Sollentuna (SE)

(73) Assignee: Xcounter AB, Daneryd (SE)

( * ) Notice: Subject to any disclaimer, the term of this patent is extended or adjusted under 35 U.S.C. 154(b) by 1178 days.

(21) Appl. No.: 11/907,474

(22) Filed: Oct. 12, 2007

(65) Prior Publication Data

US 2009/0074130 A1  Mar. 19, 2009

(30) Foreign Application Priority Data

Sep. 17, 2007  (SE) ........................................ 0702061

(51) Int. Cl.
*G06K 9/00* (2006.01)
(52) U.S. Cl. .................... 382/128; 382/131; 382/132
(58) Field of Classification Search .................. 382/128, 382/132, 103, 153, 154; 378/11, 19, 22, 378/57, 23, 37; 600/407, 472; 345/419
See application file for complete search history.

(56) References Cited

U.S. PATENT DOCUMENTS

| | | | |
|---|---|---|---|
| 4,149,247 | A | 4/1979 | Pavkovich et al. |
| 5,872,828 | A | 2/1999 | Niklason et al. |
| 6,118,125 | A | 9/2000 | Carlson et al. |
| 6,196,715 | B1 | 3/2001 | Nambu et al. |
| 6,327,330 | B1 | 12/2001 | Fritz |
| 6,337,482 | B1 | 1/2002 | Francke |
| 6,359,960 | B1 * | 3/2002 | Wahl et al. ...................... 378/20 |
| 6,373,065 | B1 | 4/2002 | Francke et al. |
| 6,385,282 | B1 | 5/2002 | Francke et al. |
| 6,411,836 | B1 | 6/2002 | Patel et al. |
| 6,414,317 | B1 | 7/2002 | Francke et al. |
| 6,476,397 | B1 | 11/2002 | Francke |

(Continued)

FOREIGN PATENT DOCUMENTS

JP  9-212633  8/1997

(Continued)

OTHER PUBLICATIONS

International-Type Search Report mailed Mar. 12, 2008 for corresponding Swedish Application No. 0702061-3.

(Continued)

*Primary Examiner* — Vikkram Bali
*Assistant Examiner* — Nancy Bitar
(74) *Attorney, Agent, or Firm* — Harness, Dickey & Pierce, P.L.C.

(57) ABSTRACT

A method for creating, displaying, and analyzing X-ray images of a plurality of objects is disclosed. The method comprising, for each of the objects recording three-dimensional X-ray image data of the object in a single measurement; creating a three-dimensional X-ray image of the object from the three-dimensional X-ray image data; creating one or two two-dimensional X-ray images of the object from the three-dimensional X-ray image data; displaying the one or two two-dimensional X-ray images of the object; and analyzing the one or two two-dimensional X-ray images of the object. For a subset of the plurality of objects the three-dimensional X-ray image of the object is displayed, wherein the subset of the plurality of objects is determined based on the step of, for each of the objects, analyzing the one or two two-dimensional X-ray images of the object.

17 Claims, 4 Drawing Sheets

U.S. PATENT DOCUMENTS

| | | | |
|---|---|---|---|
| 6,477,223 | B1 | 11/2002 | Francke |
| 6,518,578 | B1 | 2/2003 | Francke et al. |
| 6,522,722 | B1 | 2/2003 | Francke |
| 6,546,070 | B1 | 4/2003 | Francke |
| 6,600,801 | B2 | 7/2003 | Raupach |
| 6,611,575 | B1 | 8/2003 | Alyassin et al. |
| 6,823,038 | B2 | 11/2004 | Von Der Haar |
| 6,846,289 | B2 * | 1/2005 | Besson et al. ........... 600/437 |
| 6,940,942 | B2 | 9/2005 | Ullberg |
| 7,693,254 | B2 * | 4/2010 | Muller et al. ............ 378/37 |
| 2003/0194121 | A1 | 10/2003 | Eberhard et al. |
| 2004/0114709 | A1 | 6/2004 | Griffith |
| 2004/0202279 | A1 * | 10/2004 | Besson et al. ........... 378/37 |
| 2004/0249271 | A1 | 12/2004 | Besson et al. |
| 2005/0008124 | A1 | 1/2005 | Ullberg |
| 2005/0047544 | A1 | 3/2005 | Fu et al. |
| 2005/0135557 | A1 | 6/2005 | Hermann et al. |
| 2005/0219243 | A1 * | 10/2005 | Kidera ..................... 345/421 |
| 2005/0226369 | A1 * | 10/2005 | Martin et al. ............ 378/22 |
| 2006/0098855 | A1 | 5/2006 | Gkanatsios et al. |
| 2006/0100507 | A1 | 5/2006 | Mertelmeier |
| 2006/0171590 | A1 * | 8/2006 | Lu et al. .................. 382/190 |
| 2007/0189448 | A1 * | 8/2007 | Muller et al. ............ 378/37 |
| 2007/0268999 | A1 * | 11/2007 | Ullberg et al. ........... 378/21 |
| 2008/0008372 | A1 | 1/2008 | Li et al. |
| 2008/0019581 | A1 | 1/2008 | Gkanatsios et al. |

FOREIGN PATENT DOCUMENTS

| | | |
|---|---|---|
| JP | 2005-92575 | 4/2005 |
| SE | 529451 | 8/2007 |
| WO | WO 2004/107960 | 12/2004 |
| WO | WO 2006/017172 | 2/2006 |
| WO | WO 2006/055830 | 5/2006 |
| WO | WO 2008/002633 | 1/2008 |

OTHER PUBLICATIONS

International Search Report mailed Jan. 20, 2009 for corresponding International Application No. PCT/SE2008/051007.

Graeme P. Penney et al. "A Comparison of Similarity Measures for Use in 2-D-3-D Medical Image Registration". IEE Transaction on medical imaging, vol. 17, No. 4, Aug. 1998. pp. 586-595.

Internatioanl-Type Search Report mailed Dec. 20, 2006 for corresponding Swedish Application No. 0601135-7.

* cited by examiner

METHOD FOR CREATING, DISPLAYING, AND ANALYZING X-RAY IMAGES AND APPARATUS IMPLEMENTING THE METHOD

PRIORITY STATEMENT

This application claims priority under 35 U.S.C. §119 to Swedish Patent Application No. 0702061-3 filed on Sep. 17, 2007 in the Sweden Intellectual Property Office, the entire contents of which are incorporated herein by reference.

FIELD OF THE INVENTION

The invention relates generally to X-ray examination, and particularly to a method for creating, displaying, and analyzing X-ray images of a plurality of objects and to an apparatus implementing the method.

BACKGROUND OF THE INVENTION AND RELATED ART

An X-ray medical diagnostic method such as mammography or general body imaging is a low-dose procedure that creates one or more images of a part of a patient such as a breast or any other organ thereof, which is to be examined, e.g. for detection of early stages of cancer.

The mammography diagnostic procedure generally includes recording two X-ray projection images of each of the patient's breasts, one from above and one from the side. A physician or radiologist then reviews the images of the breast, i.e., mammograms, to identify any breast cancer. If the physician or radiologist finds anything that could indicate cancer the patient is recalled for a follow-up examination, during which further two-dimensional X-ray images, three-dimensional X-ray images, ultrasonic images, and/or MR images of the patient's breast are recorded, and/or cell tissues are removed for examination.

In mammography screening women of an age between about 40 and 75 years are examined by recording X-ray projection images of patients breasts each or every second year. Such procedure results in a large number of X-ray images, where only about 0.5% of the patients at each screening procedure have cancer. However, as much as about 3-15% of the patients are recalled for further examinations. Such follow-up examinations are time consuming and costly, and only a few of those will result in a cancer diagnosis.

SUMMARY OF THE INVENTION

An object of the invention is therefore to provide a method and an apparatus, respectively, by which the high number of recalled patients can be strongly reduced.

A further object of the invention is to provide a method and an apparatus, respectively, by which examinations can be made in two stages, without the need of performing new measurements between the examinations.

A still further object of the invention is to provide such method and apparatus, which are uncomplicated and can produce high-quality three-dimensional X-ray images such as three-dimensional tomosynthesis images and high-quality two-dimensional X-ray images such as two-dimensional projection images with high spatial resolution, signal-to-noise ratio, dynamic range, and image contrast, while the imaging object is exposed to a minimum of radiation.

A yet further object of the invention is to provide such method and apparatus, which are reliable, accurate, and inexpensive.

These objects, among others, are attained by methods and apparatuses as claimed in the appended claims.

According to a first aspect of the invention a method for creating, displaying, and analyzing X-ray images of a plurality of objects is provided. According to the method the following steps are performed for each of the objects: three-dimensional X-ray image data of the object are recorded in a single measurement, a three-dimensional X-ray image of the object is created from the three-dimensional X-ray image data, one or two two-dimensional X-ray images of the object are created from the three-dimensional X-ray image data, the one or two two-dimensional X-ray images are displayed, and the one or two two-dimensional X-ray images of the object are analyzed.

For each of the objects, it is determined whether that object is part of a subset of the objects based on the step of analyzing the one or two two-dimensional X-ray images of the object, and, for each object of the subset only, the three-dimensional X-ray image of the object is displayed.

The analyzing comprises preferably searching for abnormalities in the one or two two-dimensional X-ray images of the object, and the subset of the objects is determined as those objects, for which abnormalities are found in the one or two two-dimensional X-ray images.

Hereby, a single measurement can be used to form two different set of information for each object: one or two two-dimensional X-ray images, preferably projection images, and a three-dimensional X-ray image, preferably a tomosynthesis image. One set of information, i.e. the one or two two-dimensional X-ray images are displayed firstly for each object. These one or two two-dimensional X-ray images are examined, and based on such examination another set of information, i.e. three-dimensional X-ray images, are displayed for only some of the objects.

Only if an examination of the other set of information fails a further measurement of the object has to be performed. Such procedure reduces considerably the number of further measurements that have to be made.

Alternatively, two sets of three-dimensional X-ray image data of each object can be recorded, taken e.g. from two different directions through the object. For each set of three-dimensional image data, one three-dimensional image and one or two two-dimensional images are reconstructed, and the above method is, for each object, performed for each set of three-dimensional data independently of one another or in dependence on one another. For instance, the images may be displayed in the following order: one or two two-dimensional images from a first set of three-dimensional X-ray image data, one or two two-dimensional images from a second set of three-dimensional X-ray image data, a three-dimensional image from the first set of three-dimensional X-ray image data, and a three-dimensional image from the second set of three-dimensional X-ray image data. Each displaying can be made conditional on the result of an analysis of the kind disclosed herein of the previously displayed image or images.

The invention may find use in several technical fields such as baggage checking and material testing. Further, the invention is applicable to all kind of X-ray medical applications including mammography and general body examinations.

Thus, in one embodiment the objects are baggage items and the abnormalities comprise indications for weapons, explosives, and/or volatile or hazardous products.

In another embodiment the objects are pieces of a material and the abnormalities comprise indications for structure defects or similar in the material.

In yet another embodiment the objects are patients or parts thereof and the abnormalities comprise indications for pathologic structures or compositions in the patients or parts thereof. For instance, the objects may be breasts of patients and the abnormalities may comprise indications for carcinogenic structures or tumors in the breasts of the patients.

The method may be applied in a medical screening procedure, in which procedure the number of patients that have to be recalled for further measurements and examinations is heavily reduced.

According to a second aspect of the invention an apparatus implementing the method of the first aspect of the invention is provided.

Further characteristics of the invention and advantages thereof, will be evident from the detailed description of preferred embodiments of the present invention given hereinafter and the accompanying FIGS. 1-5, which are given by way of illustration only and thus, are not limitative of the present invention.

DESCRIPTION OF PREFERRED EMBODIMENTS

Figure 1:
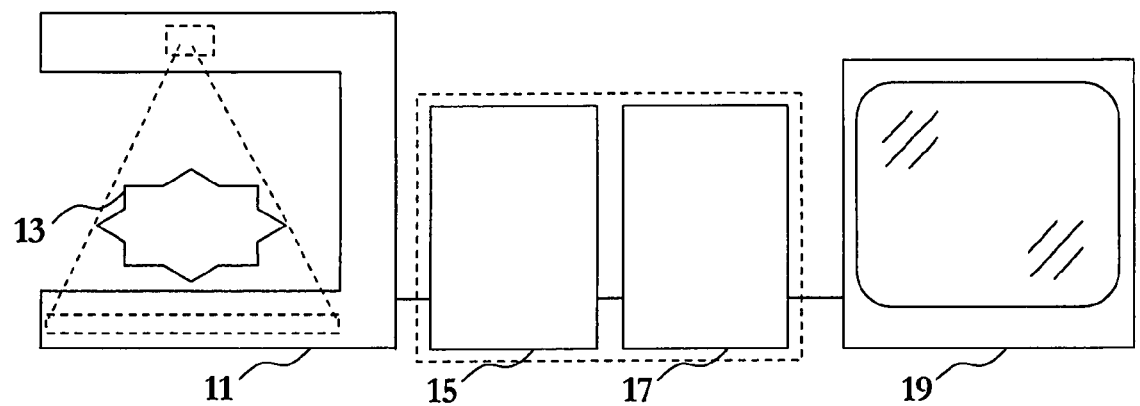
FIG. 1 illustrates schematically, in a block diagram, an apparatus for creating X-ray images of an object according to an embodiment of the present invention.

The apparatus of FIG. 1 comprises an X-ray apparatus 11 for obtaining X-ray image data of an object 13, a reconstruction device 15 for creating a three-dimensional X-ray image, preferably a three-dimensional tomosynthesis image, of the object 13 from the X-ray image data, an image construction device 17 for creating a two-dimensional X-ray image, preferably a two-dimensional projection image, of the object 13 from the three-dimensional X-ray image or from the X-ray image data, and a display device 19 for displaying the three-dimensional X-ray image and the two-dimensional X-ray image.

Figure 2:
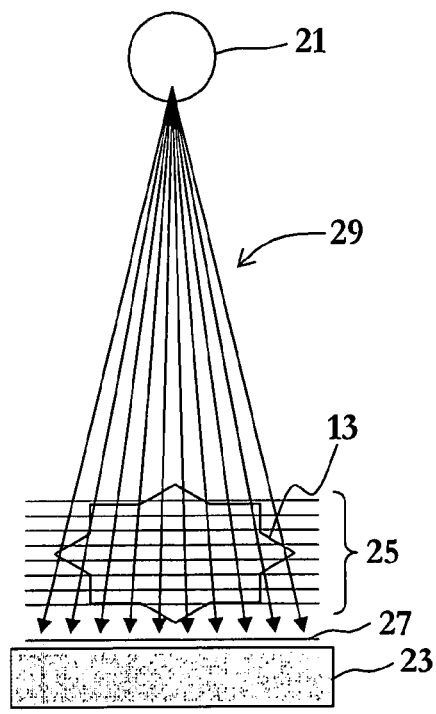
FIG. 2 illustrates how the creation of a two-dimensional projection image of an object can be performed by the apparatus of FIG. 1.

The X-ray apparatus comprises generally an X-ray source 21 and an X-ray detector 23 as being illustrated in FIG. 2 and is provided for obtaining the X-ray image data in a single measurement, in which image data is acquired at different angles. Details of how the measurement can be performed will be given further below in this description.

The reconstruction device 15 for creating a three-dimensional X-ray image of the object 13 from the three-dimensional X-ray image data may e.g. be any device known in the art. The reconstruction may be based on e.g. shift-and-add, filtered back projection, Fourier, or iterative methods for calculating the attenuation in the object 13 in three dimensions. Typically, the three-dimensional X-ray image is obtained in the shape of a stack of parallel two-dimensional images 25 as being illustrated in FIG. 2. The three-dimensional X-ray image could also be in the shape of a three dimensional model of the object segmented into three dimensional sub volumes, so called "voxels". The voxels are preferably, but necessarily placed in parallel layers parallel to the lines 25.

The image construction device 17 is arranged for creating the two-dimensional X-ray image of the object 13 e.g. by means of projecting the three-dimensional X-ray image on a first plane. Hereby, a high-quality two-dimensional X-ray image with high spatial resolution, signal-to-noise ratio, dynamic range, and image contrast is obtained.

Preferably, the two-dimensional X-ray image is formed by means of summing, for each of the pixels of the two-dimensional X-ray image 27, pixel values of pixels along a respective straight line 29 in the three-dimensional X-ray image 25 as shown in FIG. 2. The converge in a single point, which is located at a distance from the three-dimensional X-ray image 25, which is identical to the distance that the X-ray source 21 is located from the object 13 during the single measurement. This is schematically indicated in FIG. 2.

The geometry that is reconstructed is cone-shaped with an almost point-shaped X-ray source 21 at the top, from which a cone-shaped X-ray bundle of radiation is originating. The X-ray bundle traverses the object 13 and strikes the X-ray detector 23. The straight lines 29 thus coincide with the propagation path of radiation photons of the cone-shaped X-ray bundle.

If the three-dimensional X-ray image is in the form of reconstructed three dimensional model of the object, the summation could alternatively be done in any direction through the three dimensional model. For instance, the summation could be done in along parallel lines direction through the three dimensional model, e.g. perpendicular to the planes 25.

Further, the invention does not exclude that the two dimensional X-ray image is calculated in the same way as a three dimensional model of the object is calculated, but where the three dimensional model only consists of a single layer of voxels, e.g. using iterative methods for calculating the attenuation in the object 13. The attenuation of X-rays in each voxel is then a representation of the two dimensional X-ray image.

The image construction device 17 and the image construction device 17 may be integrated as different software programs, modules or subroutines in a single image processing device. Such single image processing device and/or the display device 19 may further be integrated into the X-ray apparatus 11 or may be separate devices.

Further, the image construction device 17 may be arranged for creating second two-dimensional X-ray image of the object 13 e.g. from the three-dimensional X-ray image 25 by means of the three-dimensional X-ray image on a second plane, wherein the first and second planes are non-parallel. Hereby, a second two-dimensional X-ray image of the object 13 at another view angle is obtained. Such second two-dimensional X-ray image may be of importance to the physician or radiologist, not at least in mammography applications.

Figure 3:
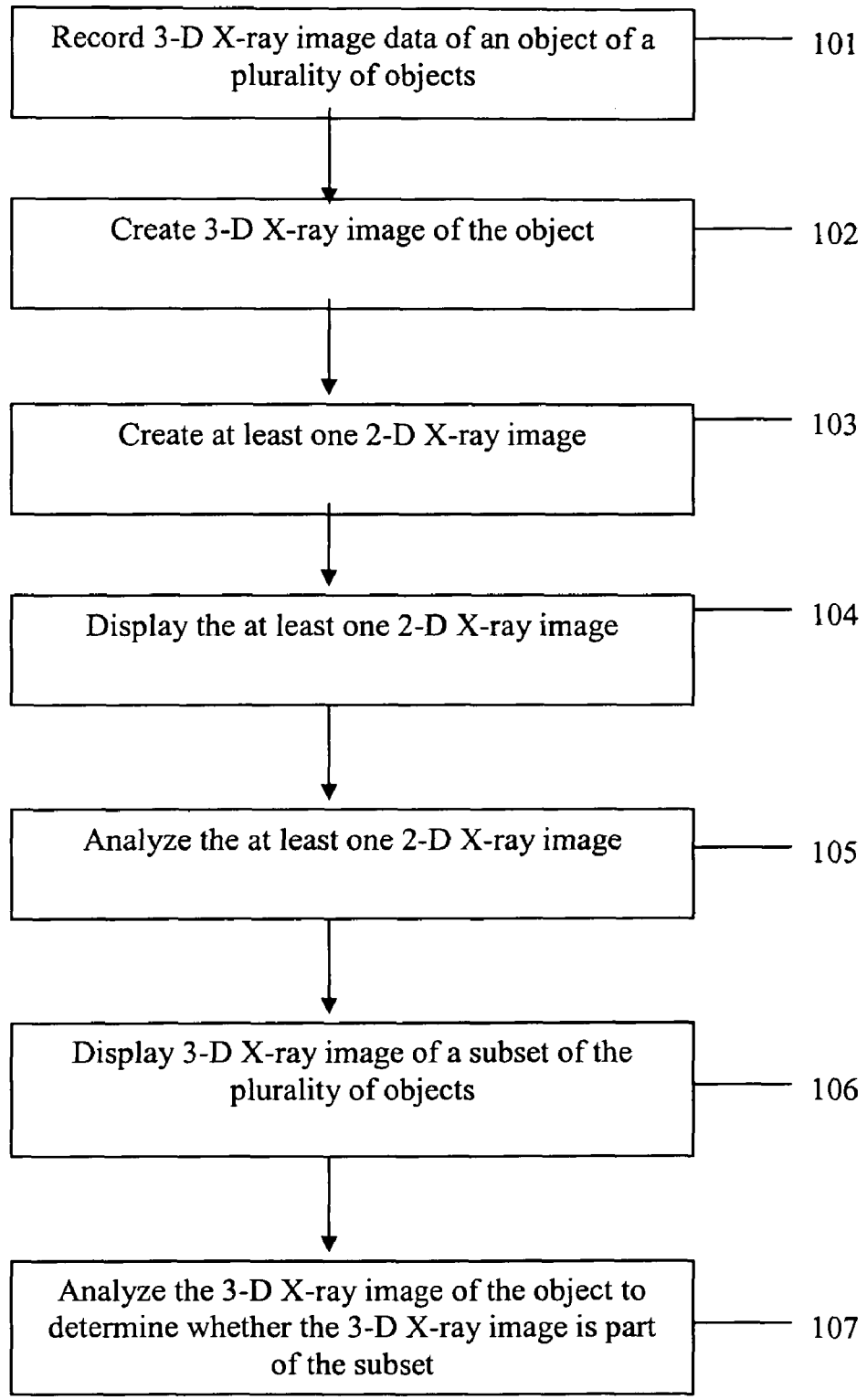
FIG. 3 is a flow scheme of a method according to an embodiment of the invention.

The apparatus thus described is provided for creating and displaying X-ray images of a plurality of objects such as breasts, bodies, baggage items or pieces of material according the following inventive algorithm, which is illustrated in FIG. 3.

For each of the objects the following actions are performed: The X-ray apparatus records, in a step 101, three-dimensional X-ray image data of the object in a single measurement. The reconstruction device creates, in step 102, a three-dimensional X-ray image 25 of the object from the three-dimensional X-ray image data and the image construction device 17 creates, in a step 103, one or two two-dimensional X-ray images 27 of the object from the three-dimensional X-ray image either directly or via the three-dimensional X-ray image. Next, the display device 19 displays, in a step 104, the one or two two-dimensional X-ray images of the object in order for a person to analyze the one or two two-dimensional images of the object. Such analysis is made in a step 105.

For each of a subset only of the objects the three-dimensional X-ray image of the object is, in a step 106 displayed, wherein for each of the objects, it is determined whether that object is part of the subset of the objects or not based on the step 105 of analyzing the one or two two-dimensional X-ray images of the object. Preferably, the algorithm ends in a step 107 by the optional step of analyzing further each of the displayed three-dimensional X-ray images.

The analyzing step 105 is preferably made, for each of the objects, by searching for abnormalities in the one or two two-dimensional X-ray images of the object, wherein the subset of the objects is determined as those objects, for which abnormalities are found in the one or two two-dimensional X-ray images of the objects.

The further analyzing step 107 is preferably made, for each of the objects of the subset of objects, by searching for abnormalities in the three-dimensional X-ray image of the object, and a further subset of the objects is determined as those objects, for which abnormalities are found in the three-dimensional X-ray image of the object, wherein the further subset of the objects are examined in a further examination.

In one embodiment the objects are baggage items and the abnormalities comprise indications for weapons, explosives, and/or volatile or hazardous products.

In another embodiment the objects are pieces of a material and the abnormalities comprise indications for structure defects in the material.

In yet another embodiment the objects are patients or parts thereof and the abnormalities comprise indications for pathologic structures or compositions in the patients or parts thereof. If the objects are breasts of patients the abnormalities may comprise indications for carcinogenic structures, tumors, or similar in the breasts of the patients.

The invention may particularly be applied in medical screening to obtain more efficient procedures. For instance, when a patient is called for examination, X-ray image data of her breasts are recorded. One or more preferably two two-dimensional X-ray images of each of her breasts are created at different view angles and are displayed for a physician. If he/she finds anything suspicious the patient has not to be recalled but a three-dimensional X-ray image is created and displayed for the physician in order to establish a diagnosis. Such procedure is here referred to as a virtual recall.

In mammography scanning all women between about 40 and 75 years are examined by X-ray imaging every or every second year, thus creating huge amounts of X-ray data and a large number of X-ray images, where only about 0.5% of the patients have cancer at each examination. After studying the two-dimensional X-ray images about 3-15% of the patients are recalled for follow-up examinations despite only a fraction of them have cancer.

The present invention is believed to considerably reduce the number of patients that have to be recalled after screening examinations, which save time and money and fewer patients have to be bothered by recalling them for follow-up examination which in most cases does not lead to any further measures.

In still another embodiment other image data, preferably ultrasonic image data, MR image data, and/or optical image data, of each of the objects are recorded simultaneously as the three-dimensional X-ray image data of the object are recorded in the step 101. Then, for each object of the subset of the objects, a further image of the object is created based on the above-mentioned other image data and is displayed either together with the three-dimensional X-ray image, in connection therewith, or after the displaying of the X-ray image. Apparatuses for use for recording such data in a single measurement are described in US 2004/0249271 and in our pending U.S. patent application Ser. No. 11/472,275, filed on Jun. 22, 2006, the contents of which being hereby incorporated by reference.

The apparatus for creating and displaying X-ray images of objects 13 comprises preferably input means e.g. a keyboard, a pointing device, or voice command receiving means (not explicitly illustrated) for receiving user selections, and the display device 19 is provided for displaying one or two two-dimensional X-ray images of an object in response to a first user selection through the input means and for displaying a three-dimensional X-ray image of the object in response to a selection through the input means. Radiologist is able to study the more X-ray image(s) firstly, and then if found, the physician may select to X-ray image. The apparatus may have means for displaying the three-dimensional X-ray image in various manners and layouts and means for displaying several three-dimensional X-ray images from different angles—one after the other or several at the same time.

In one embodiment the apparatus for creating and displaying X-ray images comprises a digital image processing device, which, for each of the objects, is provided for: analyzing the one or two two-dimensional X-ray images of the object and for finding abnormalities therein; and determining, for each of the objects, whether that object is part of the subset of the objects based on whether the abnormalities in the one or two two-dimensional X-ray images of the object are found or not.

Such digital image processing device may be a microcomputer provided with digital image processing software known in the art of digital image processing.

Thus, the apparatus for creating and displaying X-ray images may perform all steps 101-106 and the optional step 107 entirely automatically without the need of manual examination of the images.

According to a further embodiment of the method of the present invention the above method, in which the three-dimensional X-ray image data is denoted as a first set of three-dimensional X-ray image data, is accompanied, for each of the objects, by the further steps of: recording a second set of three-dimensional X-ray image data of the object in a or the single measurement; creating a three-dimensional X-ray image of the object from the second set of three-dimensional X-ray image data; creating one or two two-dimensional X-ray images of the object from the second set of three-dimensional X-ray image data; and for a subgroup only of the plurality of objects displaying the one or two two-dimensional X-ray images of the object as created from the second set of three-dimensional X-ray image data or the three-dimensional X-ray image of the object as created from the second set of three-dimensional X-ray image data, wherein for each of the plurality of objects, it is determined whether that object is part of the subgroup of the plurality of objects based on the step of analyzing the one or two two-dimensional X-ray images of the object as created from the first set of three-dimensional X-ray image data.

Yet further, the method may be generalized regarding the analyzing and displaying steps so that, for each of the object, the four image sets: (i) the one or two two-dimensional X-ray images of the object as created from the first set of three-dimensional X-ray image data, (ii) the three-dimensional X-ray image of the object as created from the first set of three-dimensional X-ray image data, (iii) the one or two two-dimensional X-ray images of the object as created from the second set of three-dimensional X-ray image data, and (iv) the three-dimensional X-ray image of the object as created from the second set of three-dimensional X-ray image data, are displayed in any given order and for all but the first image set, the displaying is made conditional on the result of an analysis performed of the previously displayed image set.

Preferably, the first and second sets of three-dimensional X-ray image data are recorded from different directions or direction ranges, angles or angle ranges, or fields of view, either simultaneously or one after the other, but before the images are displayed and analyzed.

Figure 4:
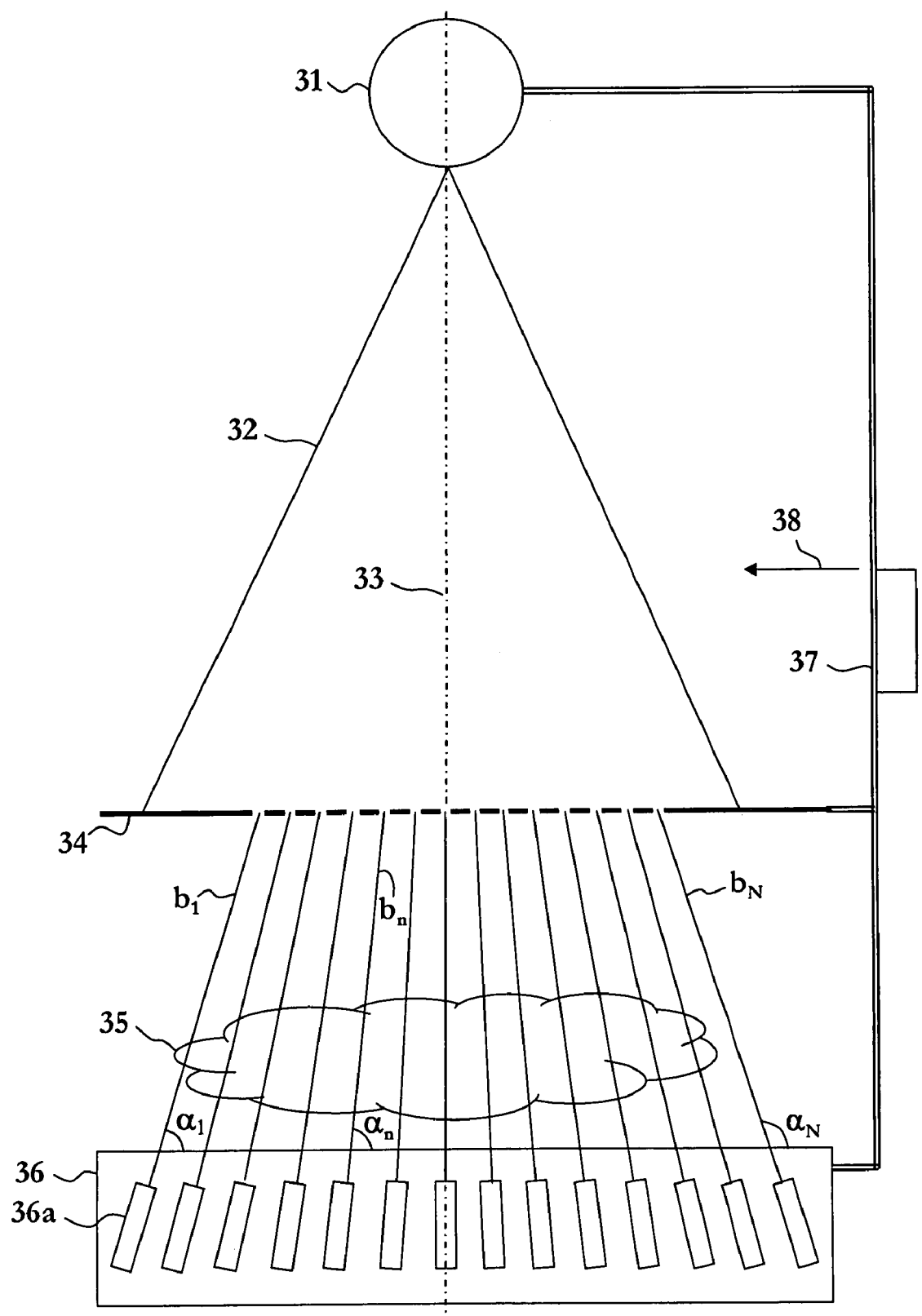
FIG. 4 illustrates schematically, in a top view, an example of an X-ray apparatus for use in the apparatus of FIG. 1.

With reference now to FIGS. 4 and 5 an example of an X-ray apparatus for use in the apparatus of FIG. 1 will briefly be described.

The X-ray apparatus comprises a divergent X-ray source 31, which produces X-rays 32 centered around an axis of symmetry 33, a collimator 34, a radiation detector 36, and a device 37, which rigidly connects the X-ray source 31, the collimator 34, and the radiation detector 36 to each other and which moves the X-ray source 31, the collimator 34, and the radiation detector 36 linearly in direction 38 essentially orthogonal to the axis of symmetry 33 to scan an object 35, which is to be examined.

The radiation detector 36 comprises a stack of line detectors 36a, each being directed towards the divergent radiation source 31 to allow a respective ray bundle $b_1, \ldots, b_n, \ldots, b_N$ of the radiation 32 that propagates in a respective one of plurality of different angles $\alpha_1, \ldots, \alpha_n, \ldots, \alpha_N$ with respect to the front surface of the radiation detector 36 to enter the respective line detector 36a.

The collimator 34 may be a thin foil of e.g. tungsten with narrow radiation transparent slits etched away, the number of which corresponds to the number of line detectors 36a of the radiation detector 36. The slits are aligned with the line detectors 36a so that X-rays passing through the slits of the collimator 34 will reach the detector units 36a, i.e. as the respective ray bundles $b_1, \ldots, b_n, \ldots, b_N$. The collimator 34, which is optional, prevents radiation, which is not directed directly towards the line detectors 36a, from impinging on the object 35, thereby reducing the radiation dose to the object 35. This is advantageous in all applications where the object 35 is a human or an animal, or parts thereof.

During scanning the device 37 moves the radiation source 31, the collimator 34, and the radiation detector 36 relative to the object 35 in a linear manner parallel with the front of the radiation detector as being indicated by arrow 38, while each of the line detectors 36a records a plurality of line images of radiation as transmitted through the object 35 in a respective one of the different angles $\alpha_1, \ldots, \alpha_n, \ldots, \alpha_N$.

The scanning may alternatively be performed by rotating the radiation source 31, the collimator 34, and the radiation detector 36 relative to the object 35. It shall also be appreciated that a similar scanning is obtained by holding the radiation source 31, the collimator 34, and the radiation detector 36 still and instead moving the object 35 to be examined.

The scanning of the object 35 is performed a length, which is sufficiently large so that each one of the line detectors 36a can be scanned across the entire object of interest to obtain, for each of the line detectors 6a, a two-dimensional image of radiation as transmitted through the object 35 in a respective one of the different angles $\alpha_1, \ldots, \alpha_n, \ldots, \alpha_N$.

Figure 5A:
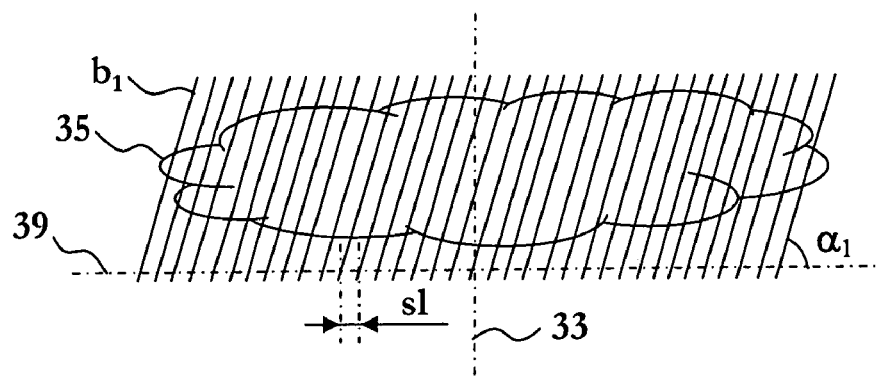
FIGS. 5a-c illustrate each schematically, in a top view, a particular X-ray bundle as it traverses the object during scanning by the X-ray apparatus of FIG. 4.
Figure 5B:
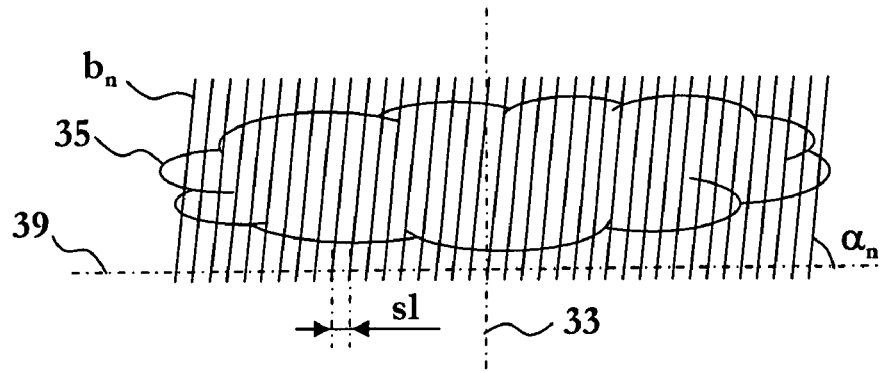
Figure 5C:
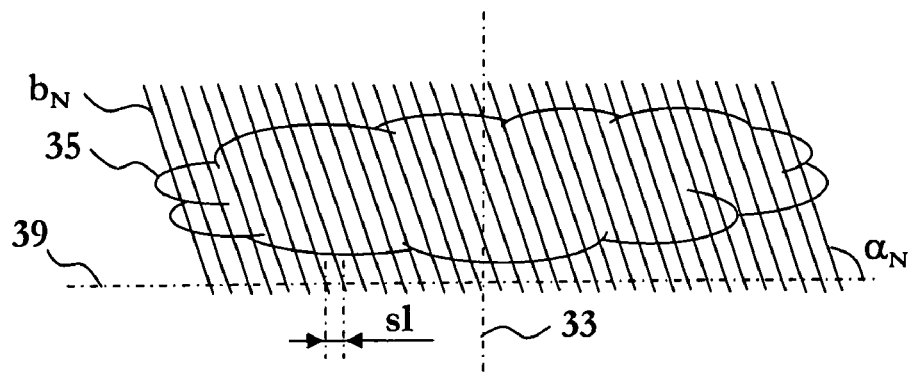

In FIGS. 5a-c three different X-ray bundles $b_1$, $b_n$, and $b_N$ are schematically illustrated as they traverse the examination object 35 during scanning by the X-ray apparatus of FIG. 4. Reference numeral 39 indicates a plane parallel with the scanning direction 38 and with the front of the radiation detector 32.

As can be seen in FIGS. 5a-c each line detector/X-ray bundle pair produces a complete two-dimensional image at a distinct one of the different angles. FIG. 5a illustrates the formation of a two-dimensional image of radiation transmitted through the object at an angle a, FIG. 5b illustrates the formation of a two-dimensional image of radiation transmitted through the same object, but at an angle $\alpha_n$, and FIG. 5c illustrates the formation of a similar two-dimensional image, but at an angle $\alpha_N$—

A preferred line detector for use in the X-ray apparatus of FIGS. 4 and 5 is a gaseous-based parallel plate detector, preferably provided with an electron avalanche amplifier. Such a gaseous-based parallel plate detector is an ionization detector, wherein electrons freed as a result of ionization by ionizing radiation are accelerated in a direction essentially perpendicular to the direction of the radiation.

For further details regarding such kind of gaseous-based line detectors for use in the present invention, reference is made to the following U.S. patents by Tom Francke et al. and assigned to XCounter AB of Sweden, which patents are hereby incorporated by reference: U.S. Pat. Nos. 6,940,942; 6,546,070; 6,522,722; 6,518,578; 6,118,125; 6,373,065; 6,337,482; 6,385,282; 6,414,317; 6,476,397; and 6,477,223.

It shall, nevertheless, be realized that any other line detector may be used in the X-ray apparatus of FIGS. 4 and 5. Such line detectors include scintillator-based arrays, CCD arrays, TFT- and CMOS-based detectors, liquid detectors, and solid-state detectors such as one-dimensional PIN-diode arrays with edge-on, near edge-on or perpendicular incidence of X-rays.

Still further, other X-ray apparatuses such as e.g. one including a two-dimensional flat panel detector for detection may be used in the apparatus of FIG. 1 and thus in the present invention. Such X-ray apparatus is rotated or tilted so that a number of two-dimensional projection images (e.g. 5-200) of the object are taken at different angles.

Devices, apparatuses and methods that can be used in the present invention further include those described in U.S. Pat. No. 6,196,715 B1; US 2005/0135557 A1; US 2005/0047544 A1; US 2005/0219243; JP 9212633; JP 2005 092575 A; and G. P. Penney et al., A Comparison of Similarity Measures for Use in 2-D-3-D Medical Image Registration, IEEE Transactions on Medical Imaging, Vol. 17, No. 4, August 1998, the contents of which being hereby incorporated by reference. Further, construction of two-dimensional X-ray images that can be employed in the present invention is detailed in our pending U.S. patent application Ser. No. 11/447,901, filed on Jun. 7, 2006, the contents of which being hereby incorporated by reference.

What is claimed is:

1. A method for creating, displaying, and analyzing X-ray images of a plurality of objects, wherein said plurality of objects are patients or parts thereof, the method being applied in a medical screening procedure and comprising:

for each object of the plurality of objects,
recording three-dimensional X-ray image data of the object in a single measurement;
creating a three-dimensional X-ray image of the object from the three-dimensional X-ray image data;
creating at least one two-dimensional X-ray image of the object from the three-dimensional X-ray image data;
displaying said at least one two-dimensional X-ray image of the object; and analyzing said at least one two-dimensional X-ray image of the object, wherein said analyzing further comprises:
  searching for abnormalities in said at least one two-dimensional X-ray image of the object, wherein said abnormalities include indications of pathologic structures or compositions in the object; and
  determining a subset of said plurality of objects as those objects for which abnormalities are found in said at least one two-dimensional X-ray image; and
for each object of the subset of said plurality of objects,
  displaying the three-dimensional X-ray image of the object; and
  determining whether said each object of the subset is part of a second subset of the plurality of objects based on an analyzing of said three-dimensional X-ray image of the object.

2. The method of claim 1 wherein, for each of the objects, said at least one two-dimensional X-ray image of the object are created from the three-dimensional X-ray image.

3. The method of claim 1, wherein said plurality of objects are baggage items and said abnormalities include indications of at least one of weapons, explosives, volatile and hazardous products.

4. The method of claim 1, wherein said plurality of objects are materials and said abnormalities include indications of structure defects in said materials.

5. The method of claim 1, wherein said plurality of objects is breasts of a patient and said abnormalities include indications of carcinogenic structures or tumors in the breasts of said patient.

6. The method of claim 1, wherein, for each of the plurality of objects, image data including at least one of ultrasonic image data, MR image data, and optical image data of the object are recorded simultaneously while said three-dimensional X-ray image data are recorded; and, for the subset of the plurality of objects, an additional image of the object is created based on the image data and said additional image of the object is displayed.

7. The method of claim 1, wherein, for each of the objects of the subset of the plurality of objects, the three-dimensional X-ray image of the object is analyzed by searching for abnormalities in said three-dimensional X-ray image of the object.

8. The method of claim 7, wherein, for each of the objects of the subset of the plurality of objects, said analyzing the three-dimensional X-ray image of the object includes,
  searching for abnormalities in said three-dimensional X-ray image of the object; and
  determining a further subset of said plurality of objects as those objects, for which abnormalities are found in said three-dimensional X-ray image of the object, wherein said further subset of said plurality of objects are examined in a further examination.

9. The method of claim 1, wherein, for each of the objects, at least two two-dimensional X-ray images are created of the object and are created to illustrate the object from different angles.

10. The method of claim 1, wherein, for each of the objects, said three-dimensional X-ray image is a tomosynthesis image and said at least one two-dimensional X-ray image is a projection image.

11. The method of claim 10, wherein, for each of the objects, said at least one two-dimensional projection image is formed by projecting the three-dimensional tomosynthesis image onto a plane by summing, for each of the pixels of the two dimensional projection image, pixel values of pixels along a respective straight line in the three-dimensional tomosynthesis image, wherein the straight lines converge in a single point.

12. The method of claim 1, wherein, for each of the objects, said three-dimensional X-ray image data is recorded by an X-ray apparatus comprising:
  a divergent radiation source emitting radiation centered around an axis of symmetry;
  a radiation detector including a stack of line detectors, each being directed towards the divergent radiation source to allow a ray bundle of the radiation that propagates in a respective one of a plurality of different angles to enter the line detector;
  an object area in a radiation path between the divergent radiation source and the radiation detector for housing the object; and
  a device configured to move the divergent radiation source and the radiation detector relative to the object in a direction essentially orthogonal to the axis of symmetry, while each of the line detectors is configured to record a plurality of line images of radiation as transmitted through the object in a respective one of the plurality of different angles, wherein
    the device is further configured to move the divergent radiation source and the radiation detector relative to the object to create a distance therebetween which is sufficient for scanning each of the line detectors across the entire object to obtain, for each of the line detectors, a two-dimensional image of radiation as transmitted through the object in a respective one of the plurality of different angles.

13. The method of claim 1, wherein, for each of the objects, said three-dimensional X-ray image data is recorded by an X-ray apparatus comprising a radiation detector including a stack of line detectors, wherein each of the line detectors is a gaseous-based ionization detector, wherein electrons emitted as a result of ionization by a respective ray bundle are accelerated in a direction essentially perpendicular to the direction of the ray bundle.

14. The method of claim 1, wherein said three-dimensional X-ray image data is a first set of three-dimensional X-ray image data, and said method comprises, for each of the objects:
  recording a second set of three-dimensional X-ray image data of the object in said single measurement;
  creating a three-dimensional X-ray image of the object from the second set of three-dimensional X-ray image data;
  creating another at least one two-dimensional X-ray image of the object from the second set of three-dimensional X-ray image data; and
  for a subgroup of said plurality of objects displaying said at least one two-dimensional X-ray image of the object as created from the second set of three-dimensional X-ray image data or said three-dimensional X-ray image of the object as created from the second set of three-dimensional X-ray image data, wherein
    for each of the plurality of objects, the method further includes determining whether the object is part of the subgroup of the plurality of objects based on the analyzing of said at least one two-dimensional X-ray image of the object as created from said first set of three-dimensional X-ray image data; and
    said first and second sets of three-dimensional X-ray image data are recorded from different directions or direction ranges.

15. An apparatus configured to implement the method of claim 1.

16. An apparatus to create and display X-ray images of a plurality of objects, wherein said plurality of objects are patients or parts thereof, the apparatus being applied in a medical screening procedure and comprising:
- an X-ray apparatus,
- an image processing device, and
- a display device, wherein, for each of the plurality of objects,
    - said X-ray apparatus is configured to record three-dimensional X-ray image data of the object in a single measurement;
    - said image processing device is configured to create a three-dimensional X-ray image of the object from the three-dimensional X-ray image data;
    - said image processing device is configured to create at least one two-dimensional X-ray image of the object from the three-dimensional X-ray image data;
    - said display device is configured to display said at least one two-dimensional X-ray image of the object;
    - said image processing device is configured to analyze said at least one two-dimensional X-ray image of the object and to find abnormalities therein, wherein said abnormalities include indications of pathologic structures or compositions in said patients or parts thereof; and
    - said image processing device is configured to determine a subset of said plurality of objects as those objects for which abnormalities are found in said at least one two-dimensional X-ray image, wherein
- said display device is, for only the subset of said plurality of objects, configured to display the three-dimensional X-ray image of the object of the subset, wherein the subset of said plurality of objects depends on, for each of the objects, abnormalities in said at least one two-dimensional X-ray image of the object,
- wherein for the subset of said plurality of objects,
    - said image processing device is configured to determine whether, for each object of the subset, the object is part of a second subset of the plurality of objects based on whether the analysis finds abnormalities in the three-dimensional X-ray images of the object.

17. The apparatus of claim 16, wherein
said display device is, for each of the plurality of objects, configured to display the at least one two-dimensional X-ray image in response to a first type of user selection via an input and, for each of the subset of the plurality of objects, the display device is configured to display the three-dimensional X-ray image in response to a second type of user selection via the input.

* * * * *